United States Patent [19]
Craig

[11] Patent Number: 5,888,390
[45] Date of Patent: *Mar. 30, 1999

[54] MULTILAYER INTEGRATED ASSEMBLY FOR EFFECTING FLUID HANDLING FUNCTIONS

[75] Inventor: Stephen R. Craig, Wilmington, Del.

[73] Assignee: Hewlett-Packard Company, Palo Alto, Calif.

[*] Notice: This patent issued on a continued prosecution application filed under 37 CFR 1.53(d), and is subject to the twenty year patent term provisions of 35 U.S.C. 154(a)(2).

[21] Appl. No.: 845,974

[22] Filed: Apr. 30, 1997

[51] Int. Cl.$^6$ .................................................. B01D 15/08
[52] U.S. Cl. ....................... 210/198.2; 210/656; 204/451; 204/601; 422/70
[58] Field of Search ..................... 210/635, 656, 210/659, 198.2; 204/601, 602, 603, 604, 605, 451, 452, 453, 454; 422/68.1, 69, 70

[56] References Cited

U.S. PATENT DOCUMENTS

| | | | |
|---|---|---|---|
| 3,530,568 | 9/1970 | Owczarski et al. | 29/35 |
| 3,538,744 | 11/1970 | Karasek | 73/23.1 |
| 3,678,570 | 7/1972 | Paulonis et al. | 29/498 |
| 4,220,276 | 9/1980 | Weisert et al. | 228/118 |
| 4,245,769 | 1/1981 | Meginnis | 228/173 B |
| 4,474,889 | 10/1984 | Terry et al. | 436/161 |
| 4,551,251 | 11/1985 | Kolobrow | 210/635 |
| 4,891,120 | 1/1990 | Serhi et al. | 204/299 R |
| 4,905,497 | 3/1990 | Shindo et al. | 73/1 G |
| 4,908,112 | 3/1990 | Pace | 204/299 R |
| 4,935,040 | 6/1990 | Goedert | 55/197 |
| 5,116,495 | 5/1992 | Prohaska | 210/198.2 |
| 5,132,012 | 7/1992 | Miura et al. | 210/198.2 |
| 5,194,133 | 3/1993 | Clark et al. | 204/299 R |
| 5,236,118 | 8/1993 | Bower et al. | 228/193 |
| 5,453,769 | 9/1995 | Schantz et al. | 347/63 |
| 5,500,071 | 3/1996 | Kaltenbach et al. | 156/272.8 |
| 5,567,868 | 10/1996 | Craig et al. | 73/23.42 |
| 5,571,410 | 11/1996 | Swedberg et al. | 210/198.2 |
| 5,595,650 | 1/1997 | Manz | 210/657 |

Primary Examiner—Ernest G. Therkorn
Attorney, Agent, or Firm—Mark Z. Dudley

[57] ABSTRACT

A multilayer integrated assembly for effecting fluid handling functions includes complementary microstructures formed by an etching or similar process in a planar foldable substrate. The complementary microstructures may be superimposed in a controlled manner by operation of microalignment means also formed in the foldable substrate by an etching or similar process. Microstructures are contemplated as including channels (that may be superimposed to form fluid conduits), apertures, conduit apertures, sample processing compartments, and the like. The resulting integrated assembly may be bonded and subsequently operated to implement one or more fluid-handling functions.

25 Claims, 9 Drawing Sheets

MULTILAYER INTEGRATED ASSEMBLY FOR EFFECTING FLUID HANDLING FUNCTIONS

FIELD OF THE INVENTION

The present invention relates generally to miniaturized planar device technology for liquid and gas phase analysis. More particularly, the invention relates to a multilayer integrated assembly for effecting fluid handling functions.

BACKGROUND OF THE INVENTION

In sample analysis instrumentation, and especially in separation systems such as gas or liquid chromatography and capillary electrophoresis systems, smaller dimensions will generally result in improved performance characteristics and at the same time result in reduced production and analysis costs. In this regard, miniaturized planar devices provide more effective system design and result in lower overhead due to decreased instrumentation sizing. Additionally, miniaturized planar devices enable increased speed of analysis, decreased sample and solvent consumption and the possibility of increased detection efficiency.

Several approaches towards miniaturization have developed in the art. The conventional approach provides etched planar devices on glass, silica, metal, or ceramic substrates of moderately small size. For example, planar devices may be etched in a wafer that receives a superimposed cover plate. In some approaches, certain fluid handling functions have not been integrated in the planar device and accordingly must be effected by use of conventional devices, such as fused silica capillary tubing, that are attached to the planar device. More recent approaches have used micromachining of silicon substrates and laser ablation of organic nonmetallic substrates to provide structures of much smaller size (i.e., microstructures) on the substrate. For example, there has been a trend towards providing planar systems having capillary separation microstructures. See, for example: Karasek, U.S. Pat. No. 3,538,744; Terry et al., U.S. Pat. No. 4,474,889; Goedert, U.S. Pat. No. 4,935,040; Sethi et al., U.S. Pat. No. 4,891,120; Shindo et al, U.S. Pat. 4,905,497; Miura et al., U.S. Pat. No. 5,132,012. See, also, attempts at miniaturization with respect to: gas chromatography (widmer et al. (1984) Int. J. Environ. Anal. Chem. 18:1), high pressure liquid chromatography (Muller et al. (1991) J. High Resolut. Chromatogr. 14:174; Manz et al. (1990) Sensors & Actuators B1:249; Novotny et al., eds. (1985) Microcolumn Separations: Columns, Instrumentation and Ancillary Techniques (J. Chromatogr. Library, Vol. 30); Kucera, ed. (1984) Micro-Column High Performance Liquid Chromatography, Elsevier, Amsterdam; Scott, ed. (1984) Small Bore Liquid Chromatography Columns: Their Properties and Uses, Wiley, N. Y.; Jorgenson et al. (1983) J. Chromatogr. 255:335; Knox et al. (1979) J. Chromatogr. 186:405; Tsuda et al. (1978) Anal. Chem. 50:632) and capillary electrophoresis (Manz et al. (1992) J. Chromatogr. 593:253; Manz et al. Trends Anal. Chem. 10:144; Olefirowicz et al. (1990) Anal. Chem. 62:1872; Second Int'l Symp. High-Perf. Capillary Electrophoresis (1990) J. Chromatogr. 516; Ghowsi et al. (1990) Anal. Chem. 62:2714.

Micromachining techniques applied to silicon utilize a number of established techniques developed by the microelectronics industry involving micromachining of planar materials, such as silicon. Micromachining silicon substrates to form miniaturized separation systems generally involves a combination of film deposition, photolithography, etching and bonding techniques to fabricate three-dimensional microstructures. Silicon provides a useful substrate in this regard since it exhibits high strength and hardness characteristics and can be micromachined to provide structures having dimensions in the order of a few micrometers. Examples of the use of micromachining techniques to produce miniaturized separation devices on silicon or borosilicate glass chips can be found in U.S. Pat. No. 5,194,133 to Clark et al.; U.S. Pat. No. 5,132,012 to Miura et al.; in U.S. Pat. No. 4,908,112 to Pace; and in U.S. Pat. No. 4,891,120 to Sethi et al.; Fan et al., Anal. Chem. 66(1):177–184 (1994); Manz et al., Adv. Chrom. 33:1–66 (1993); Harrison et al., Sens. Actuators, B10 (2): 107–116 (1993); Manz et al., Trends Anal. Chem. 10 (5): 144–149 (1991); and Manz et al., Sensors and Actuators B (Chemical) B1 (1–6): 249–255 (1990).

A drawback in the silicon micromachining approach to miniaturization involves the chemical activity and chemical instability of silicon dioxide ($SiO_2$) substrates, such as silica, quartz or glass, which are commonly used in systems for both capillary electrophoresis (CE) and chromatographic analysis systems. More particularly, silicon dioxide substrates are characterized as high energy surfaces and strongly adsorb many compounds, most notably bases. The use of silicon dioxide materials in separation systems is further restricted due to the chemical instability of those substrates, as the dissolution of $SiO_2$ materials increases in basic conditions (at pH greater than 7.0).

Accordingly, Kaltenbach et al., in commonly-assigned U.S. Pat. No. 5,500,071, and Swedberg et al., in commonly-assigned U.S. Pat. No. 5,571,410 disclose a miniaturized total analysis system comprising a miniaturized planar column device for use in a liquid phase analysis system. The miniaturized column device is provided in a substantially planar substrate, wherein the substrate is comprised of a material selected to avoid the inherent chemical activity and pH instability encountered with silicon and prior silicon dioxide-based device substrates. More specifically, a miniaturized planar column device is provided by ablating component microstructures in a substrate using laser radiation. The miniaturized column device is described as being formed by providing two substantially planar halves having microstructures thereon, which, when the two halves are folded upon each other, define a sample processing compartment featuring enhanced symmetry and axial alignment.

However, although the foregoing techniques are useful in the fabrication of miniaturized planar devices for effecting fluid handling functions in sample analysis systems, there are significant disadvantages to the prior art approaches. One significant problem remains in providing exact alignment of complementary pairs of microstructures that are respectively provided in a planar substrate and its cover plate, or in a pair of planar substrates, when such microstructures are intended to be superimposed so as to subsequently be capable of performing a fluid handling function in a unitary assembly.

For some applications, prior art planar technology has not produced a sufficient degree of alignment between the superimposed microstructures. For example, and with reference to FIG. 1A, first and second substrates 51, 52 are each shown to include spaced channels 53, 54 that are etched or otherwise formed in respective surfaces 55, 56. Superposition and appropriate bonding of the surfaces 55, 56 is intended to result in exact alignment of the channels 53, 54 such that respective fluid handling channels 61–65 are created, each of which are intended to exhibit a uniform, consistent cross-section along the major axis of the channel. However, and as illustrated, the shortcomings of the prior art result in channels on one substrate that are subject to variation in their location with respect to their complementary channels on a second, complementary substrate, thus evidencing misalignment of the channels when the substrates are superimposed. The misalignment is sufficient such that the resulting conduits (such as conduits 62–64) are subject to substantial irregularity, and in extreme cases (such as exemplified by conduit portions 65, 66) the channels are not fully integrated.

As shown in FIG. 1B, first and second substrates 71, 72 are each shown to include spaced channels 73, 74 that are etched or otherwise formed in respective surfaces 75, 76 by conventional techniques. Superimposition and appropriate bonding of the surfaces 75, 76 may succeed in adequate alignment of the channels 73, 74 such that respective fluid handling conduits 81–83 are created. However, deficiencies in many of the conventional techniques for forming the channels 73, 74 can result in edge effects and other asperities that create undesirable defects 78 in the channels 81–83. These defects 78 retard fluid flow and create localized reservoirs of fluid; accordingly, the defects 78 degrade the efficiency and uniformity of fluid flowing in the channels 81–83; the defects 78 also degrade the separation efficiency of a channel that is used to construct a separation column.

Another significant problem arises in the attempt to effect hermetic sealing of the superimposed surfaces 75, 76. This step is generally carried out using adhesives which may not fully isolate the conduits 81–83, thus resulting in cross-conduit leakage. Conventional surface bonds may be prone to failure, leakage, or to degradation induced by adverse conditions, such as high temperature environments, or by the destructive nature of certain gases or liquids that may be present in the channels.

Further, silicon substrates, and most ablatable materials such as polyimides, do not offer a sufficient combination of thermal and mechanical characteristics that otherwise would make the substrate as useful in certain applications as the named alternative materials. For instance, silicon materials are not ductile and cannot be folded, shaped, etc.; ablatable materials exhibit a low coefficient of thermal conductivity and are not susceptible to rapid and uniform heating or cooling, nor do they offer sufficient strength or ductility such that an ablatable substrate may be configured as a connecting member, housing, or support for other components in a sample analysis system. Furthermore, ablatable materials are expressly selected for their propensity to ablate upon the application of heat, and thus are not considered to be as robust and impervious to adverse (e.g., high-temperature) environments in comparison to metals and metal alloys.

SUMMARY OF THE INVENTION

The present invention relates to a multilayer integrated assembly (hereinafter, "integrated assembly") for effecting fluid handling functions for use in a gas or liquid phase sample analysis system.

In one aspect of the invention, an integrated assembly useful in, e.g., sample analysis systems, may be constructed according to the invention wherein complementary microstructures are formed by an etching or similar process in a planar substrate. Accordingly, the complementary microstructures may be superimposed in a controlled manner by operation of micro-alignment means also formed in the substrate by an etching or similar process. Microstructures are contemplated as including channels (that may be superimposed to form fluid conduits), apertures, conduit apertures, sample processing compartments, and the like. The resulting integrated assembly may be operated to implement one or more fluid-handling functions.

It is a primary feature of the present invention to construct the integrated assembly from a planar substrate having at least first and second component sections separated by a linear fold means, wherein said substrate is comprised of a material that is ductile in the region of the linear fold means and substantially inextensible in the regions defined by the component sections. The preferred substrate material also exhibits appropriate thermal and mechanical characteristics such that the component sections of the substrate may be superimposed by folding the substrate at the linear fold means, then bonded and optionally shaped to provide a unitary assembly having a useful configuration.

More specifically, it is contemplated herein to provide the integrated assembly by etching complementary microstructures in the planar substrate prior to folding by using conventional photolithography and etching techniques. In the preferred embodiment, an integrated assembly is formed by providing a planar substrate having at least first and second adjacent component sections having a respective first and second complementary microstructures etched thereon. The adjacent component sections are separated by a linear fold means (also, preferably, provided in the substrate during the provision of the microstructures) and extend transversely from a fold axis defined by the linear fold means. The planar substrate is composed of a ductile material in the immediate vicinity of the linear fold means, yet is generally inextensible in the component sections, such that the two adjacent component sections may be superimposed by folding the component sections upon each other about the fold axis. Upon superimposition of the component sections, the first and second complementary microstructures are precisely co-located and superimposed. The fold means constrains the co-location of the microstructures with extreme accuracy due to the inextensibility of the substrate with respect to the fold axis. Thus the complementary microstructures are joined with precise alignment.

In another aspect of the invention, a specialized intermediary substrate may be interposed between the mating surfaces.

In another aspect of the invention, a particularly preferred multilayer integrated assembly includes n component sections and (n–1) linear fold means, wherein n equals three or more, wherein the component sections are closed upon one another in a Z-fold configuration.

In another aspect of the present invention, the preferred substrate materials are especially susceptible to subsequent bonding of the component sections via diffusion bonding to provide a unitary integrated assembly. A preferred diffusion bonding process in this invention contemplates the step of initially electroplating the surfaces to be joined with a very thin surface layer. The integrated assembly is then heated in vacuum to a bonding temperature above the liquidus temperature of the nickel-base surface layer on the component sections being bonded. At this temperature the surface layer melts and a thin layer of liquid alloy wets and fills the gaps and other asperities between the two mating surfaces. The flow of the surface layer in its molten state during the joining operation allows the component sections to be bonded in such a way as to correct the irregularities, asperities, or other possible deleterious structural aspects in the mating surfaces. In particular, such flow will correct many of the defects that may be present in the interface of complementary microstructures, thus rendering the microstructures more useful.

In the practice of the invention, a preferred substrate material comprises a metal or metal alloy, such as steel and especially stainless steel. Further, the preferred substrate may be produced in long plates. A removable support means situated at the sides of the substrate may be provided to accurately and securely transport the substrate through a manufacturing process and easily allow batch mode processing of plural component sections on a single substrate.

In a preferred embodiment of the invention, channels of a semi-circular cross section are etched by controlling the etch process. Accordingly, when a corresponding semi-circular channel is aligned with a channel thus formed, a fluid-handling structure of highly symmetrical circular cross-section is defined which may be desirable for enhanced fluid flow through, for example, a fluid circuit in a sample processing or sample analysis system.

ADVANTAGES OF THE INVENTION

Use of a linear fold means in a foldable substrate material to form the integrated assembly affords several advantages over prior etching, ablation, and micromachining techniques used to form microstructures for fluid handling systems. The application of computerized control over the lithographic process allows the fold means to define, with great precision, a fold axis that is located equidistant from the complementary microstructures, thereby enabling a heightened degree of alignment of the complementary microstructures when the assembly is integrated by superimposing and bonding the component sections.

An intermediary substrate is contemplated as being a useful addition to the integrated assembly so as to provide a useful characteristic that differs from the characteristics in substrate used to provide the foldable substrate. Accordingly, a intermediary substrate may be included to expand the functionality of the integrated assembly. In addition, the intermediary substrate may offer a surface treatment, structure, or function that is difficult or impractical to provide in the substrate but which can be effectively provided in the material used to fabricated the intermediary substrate.

In another advantage of the invention, bonding of the superimposed component sections is preferably accomplished by use of a diffusion bonding technique. In a particular embodiment of the preferred diffusion bonding process, the diffusion bonding is effected utilizing a thin alloy plated layer which melts at the desired diffusion bonding temperature, forming a transient liquid phase that is interposed in the interface of the abutted surfaces of the component sections. The transient liquid phase subsequently re-solidifies at temperature as a result of constituent inter-diffusion. Continued heat treatment may be employed to provide a homogeneous solid-state diffusion bond. The flow of the surface layer in its molten state during the joining operation allows the component sections to be be bonded in such a way as to correct the irregularities, asperities, or other possible deleterious structural aspects in the mating surfaces. In particular, such flow will correct many of the defects that may be present in the interface of complementary microstructures, thus rendering the microstructures more useful.

In particular, the preferred diffusion bonding process for the integrated assembly may be understood to include heating the assembly in a vacuum (approximately $10^{-5}$ torr) to the desired bonding temperature above the liquidus temperature of the nickel-base surface layer on the component sections being bonded (typically in the range of 900–1000 degree(s) F.) At this temperature the surface layer melts and a thin layer of liquid alloy wets and fills the gaps and other asperities (see, for example, FIG. 1B) between the two mating surfaces. While the assembly is held at temperature, rapid diffusion of certain alloying elements occurs between the molten alloy and the base metal, resulting in a compositional change at the joint. This change raises the local melting point and causes the joint to isothermally solidify thus creating the initial bond. Upon completion of the initial isothermal solidification (typically in 1–3 hours), the joint microstructure resembles that of the base metal except for some compositional and structural heterogeneity. Additional steps may optionally be employed in continuation of the heat treatment at temperature for a time sufficient to completely homogenize the joint region so that, ultimately, it reaches a composition corresponding or at least closely equivalent to the base metal, although a separate and distinct subsequent heat treatment may be utilized. After completion of the bonding process, the bonded assembly can then be given whatever further heat treatments are required for strengthening or in fulfillment of coating requirements.

The preferred diffusion bonding process of this invention contemplates initially electroplating the surfaces to be joined with a very thin nickel-base surface layer, that is, a layer of nickel, nickel-phosphorous, or a nickel-cobalt alloy.

In a particular advantage of the invention, the flow of the surface layer in its molten state during the joining operation allows parts of complex geometry to be bonded in such a way as to correct the irregularities, asperities, or other possible deleterious structural aspects in the mating surfaces. Such flow will correct many of the defects that may be present in the interface of complementary microstructures, thus rendering the microstructure more useful.

Preferably the surface layer is composed of an alloy that is formulated to melt at a temperature at which the base metal (in the foldable substrate) can be exposed without deleterious effect but must be such that, in terms of composition and thickness, solidification will occur at temperature, and chemical and microstructural homogeneity may be achieved in a practical processing time. Various melting point depressants such as phosphorous, boron, silicon, manganese, columbium and titanium are possible. Several combinations of these elements with nickel produce surface layers with satisfactory melting points. However, as disclosed in U.S. Pat. No. 3,678,570, some depressants except boron may produce unwanted stable phases at the joint interface.

Satisfactory bonds have been obtained between component sections in a foldable substrate formed of 316L stainless steel utilizing the foregoing process parameters and a surface layer of nickel-phosphorous alloy on the component sections. The resulting bond lines were found to be nearly indistinguishable; more importantly, the asperities in the edges at joints between superimposed channels were filled and accordingly indistinguishable, even after transversely sectioning the integrated assembly and subjecting the sectioned channels to microscopic analysis.

In another advantage of the invention, the integrated assembly will be seen to facilitate reliable connections between external fluid-handling functional devices (such as fittings, valves, sensors, and the like) by use of a single planar device for the provision of a plurality of flow paths. The fluid-handling functional devices that connect to the integrated assembly are preferably constructed to be surface-mounted, which has been found to offer reliable, fluid-tight connection without the complexity and difficulty of conventional connections. The number and complexity of external connections, which would otherwise undesirably increase the volume of the flow system, are also decreased. Another advantage is that the reliability of the fluid-bearing connections is improved.

A further advantage of the present invention is that an integrated assembly and multiple fluid-handling functional devices may be coordinated and assembled in a smaller volume than is possible in prior art systems. This results from the pneumatic channels that are integrated in the integrated assembly, and thus many of the fluid flow paths are integral to the integrated assembly, which is itself quite compact and amenable to construction in a variety of shapes and configurations. For example, it is contemplated that the integrated assembly may be constructed in an irregular shape, such as a curved, bent, or angled configuration, so as to conform to an irregularly-shaped, compact volume.

A large number of fluid-handling functional paths may be integrated into the integrated assembly that heretofore would be difficult if not impossible to assemble using traditional tubular pipe, ferrules, and manual fittings. Also, considerable cost savings and improved reliability are realized by reduction of the number of connections necessary to achieve multiple flow paths.

The surface-mounted pneumatic connections provided by the invention also reduce the complexity of a flow system, which is desirable during the stages of manufacturing, assembly, repair, or modification of the analytical instrument in which the integrated assembly may be situated.

A particular advantage of the present invention is the use of processes other than silicon micromachining techniques or etching techniques to create microstructures in a metallic or metal alloy substrates having desirable attributes for an analysis portion of a sample analysis system. The use of conventional etching processes to form microstructures in the preferred substrate materials, such as metal alloys, increases the ease of fabrication and lowers the per-unit manufacturing costs in the subject devices as compared to prior approaches, such as micromachining devices in silicon. The integrated assembly is robust (e.g., exhibits an ability to withstand adverse environments, mishandling, and operation at elevated temperature), is easily cooled or heated, and is sufficiently strong and rigid so as to serve as a connecting member, support member, chassis, housing, or the like. In this regard, devices formed according to the invention in the preferred substrates have the added feature of being robust yet quite inexpensive, and thus capable of use as substantially disposable miniaturized assemblies.

In another aspect of the instant invention, formation of the integrated assembly in the preferred substrate material allows for configuration of the integrated assembly in almost any geometry or shape. This feature not only enables the formation of complex device configurations, but further allows for integration of sample preparation, sample injection, post-column reaction, and sample detection means in a miniaturized sample analysis system having greatly reduced overall dimensions. The compact nature of the analysis portion in a system produced under to the present invention, in conjunction with the feature that integral functions such as injection, sample handling and detection may be specifically engineered into the subject device to provide a sample analysis device, further allows for an improvement in the degree of system integration, thus also accomplishing an inexpensive miniaturized system.

In this regard, a miniaturized analytical system constructed according to the present invention is capable of performing complex fluid handling methods with reduced attention by an operator. The integrated assembly may have as mounted thereon associated fluid-handling functional devices, such as inlet means, valve means, detection means, and temperature control means. The resulting planar module occupies a more compact volume as compared to fluid handling systems constructed according to conventional technology.

Accordingly, the subject invention finds potential application in monitoring and/or analysis of components in chemical, biological, biochemical, pharmaceutical, and medical processes and the like.

DETAILED DESCRIPTION OF THE INVENTION

Figure 1A:
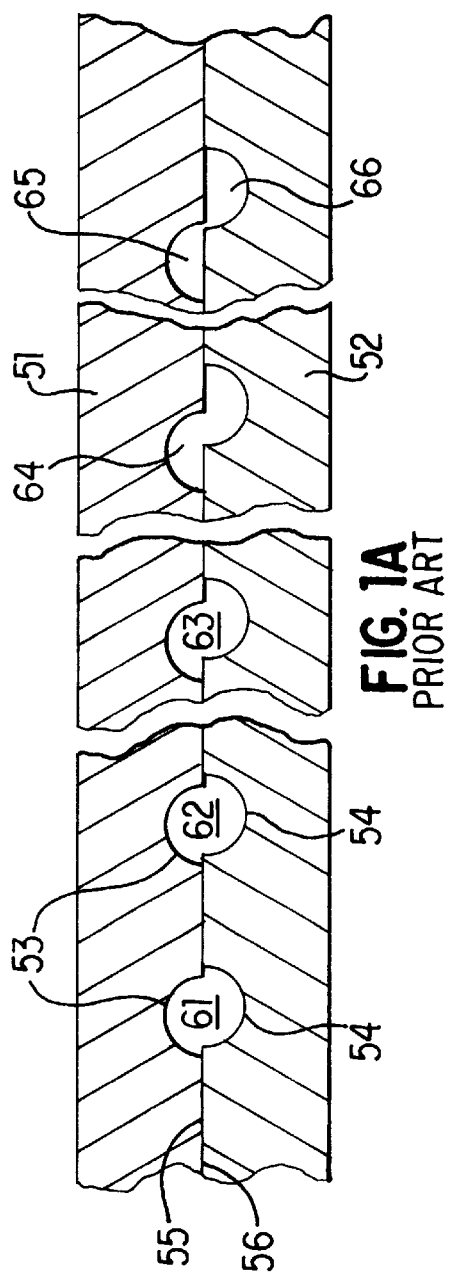
FIGS. 1A and 1B are simplified, side sectional views of a planar device incorporating fluid channels that is constructed in accordance with the prior art.
Figure 1B:
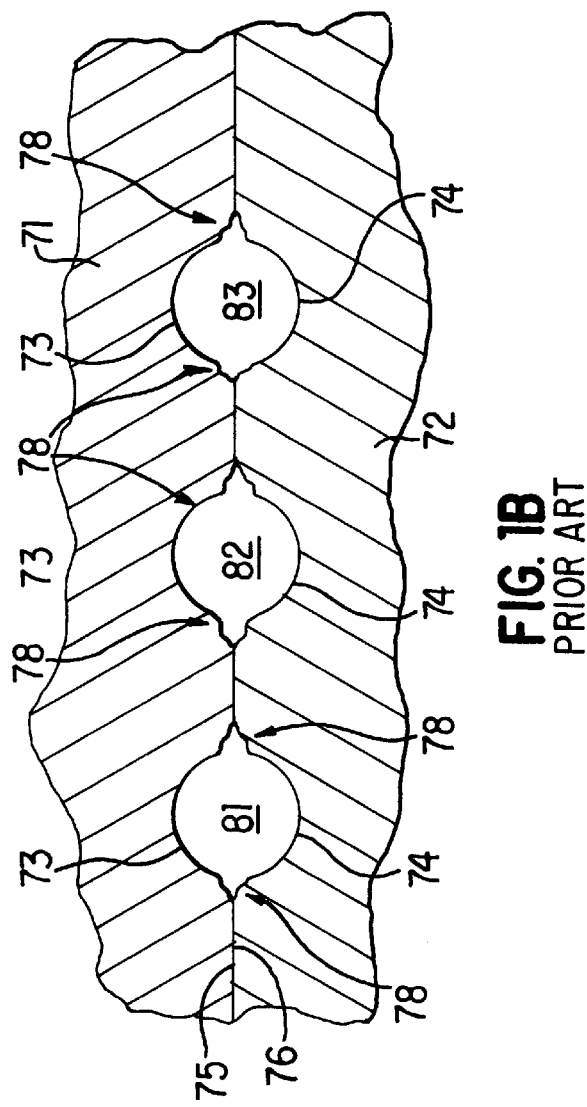

Before the invention is described in detail, it is to be understood that the invention is not limited to the particular component parts of the devices described or process steps of the methods described, as such devices and methods may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "an analyte" includes mixtures of analytes, reference to "a detection means" includes two or more such detection means, reference to "a sample flow component" includes more than one such component, reference to "an on-device fluid reservoir compartment" includes two or more such compartments, and the like. In this specification and in the claims which follow, reference will be made to a number of terms which shall be defined to have the following meanings:

The use of novel construction and assembly techniques in the practice of the invention allows for a high degree of precision in the alignment of surface features other structures, which alignment has either been difficult or not possible in prior substrate-based devices. Thus, the term "microalignment" as used herein refers to precise alignment of structures, microstructures, and other surface features, including: the enhanced alignment of apertures, complementary channels, or compartments with each other; of inlet and/or outlet ports with channels or separation compartments; of detection means with ports, channels or separation compartments; and of detection means with other detection means, and the like. The precision in alignment offered by the practice of the invention is believed to be on the order of less than one micrometer of error. In some instances, the microalignment has been so precise that alignment error is indistinguishable even under microscopic examination of transverse sections of bonded microstructures.

The terms "surface feature" refer to a structural feature on a component section that is distinguishable from the immediately surrounding portion of the component section. Examples of a surface feature include: aperture, recess, perforation, orifice, groove, chamber, compartment, depression, channel, pad, block, protrusion, nipple, and region (especially a region having a surface treatment). Note that the shape, dimensions, and symmetry of the various surface features contemplated herein will vary according to the implementation of the invention.

"Microstructures" refers to surface features in the component sections having dimensions on the order of approximately 5 to 1000 micrometers and may include microchannels, microapertures, depressions, and the like. Microstructures in the form of microchannels of a semicircular cross section are etched by controlling the etch process. When a first channel is microaligned with a second channel thus formed, a fluid-handling conduit of highly symmetrical circular cross-section is defined which may be desirable for enhanced fluid flaw in, for example, a sample processing or sample analysis system. Note that the shape, dimensions, and symmetry of the various microstructures contemplated herein will vary according to the implementation of the invention.

The terms "linear fold means" refer to means for dividing a substrate into at least two component sections whereby the operation of the linear fold means allows microalignment of complementary surface features in the component sections. Linear fold means can be formed in the substrate either by etching or by other methods of fabricating shaped apertures or depressions. Representative linear fold means that can be employed herein include a plurality of co-axially arranged apertures in component parts and/or a plurality of corresponding features in the substrate, e.g., depressions, grooves, slots, tunnels, hollow ridges, or the like. Accurate microalignment of two or more component sections is effected by forming at least one linear fold means provided between adjacent pairs of component sections, such that each pair of the component sections have surfaces that can be folded to overlie each other thereby forming composite micro-scale features such as apertures, compartments, or channels. Such linear fold means is preferably embodied by a row of spaced-apart perforations etched in a particular substrate, or by spaced-apart slot-like depressions or apertures etched so as to extend only part way through the substrate. The perforations or depressions can have circular, diamond, hexagonal or other shapes that promote hinge formation along a predetermined straight line.

The linear fold means preferably includes a "fold relief" which refers to a relief or similar excision of the substrate that facilitates folding of the substrate and the subsequent microalignment of the microstructures while maintaining the inextensibility of the substrate. The fold relief is effective at relieving the stress or deformation induced in the substrate in the immediate area of the fold axis by the folding motion.

The terms "foldable substrate" refer to a substrate which includes linear fold means, at least first and second component sections so defined by the linear fold means, and a characteristic of being foldable about the fold axis such that the substrate material is substantially inextensible in the direction generally transverse to the fold axis. As a result, the microalignment of surface features upon closure of the component sections is maintained due to the lack of extension of the foldable substrate.

The term "substantially inextensible" is used herein to refer to a characteristic physical nature of a foldable substrate material that resists extension from the fold axis when the foldable substrate is subject to the typical forces which it is expected to receive during the assembly and use of an integrated assembly. Accordingly, miniaturized column devices are formed herein using suitable substrates which exhibit inextensibility when folded, such as metals and metal alloy substrates.

The terms "etched" and "etching" refer to surface material removal processes and include machining or cutting processes that provide surface features in a suitable substrate that are comparable to etched features. Etching is a preferred method for forming surface features in a wide variety of geometries. Any geometry which does not include undercutting may be provided using etching techniques. However, other forming methods for providing surface features are also contemplated, such as coining, fine blanking, milling, and abrading (using an abrasive in, e.g., an air or water stream.)

Etching includes such processes as common photolithography. Under the present invention, surface features are formed by imaging a lithographic mask onto a suitable substrate and then etching the substrate in areas that are unprotected by the lithographic mask. Such masks may define all of the etched features for a selected area of the substrate, for example, and the pattern may encompass multiple pairs of component sections to be created on the substrate, each of which feature complementary sets of microstructures. Alternatively, individual patterns such as an aperture pattern, a channel pattern, etc., may be placed side by side on a common mask for stepwise exposure of large substrates which are eventually processed to produce a plurality of individual substrates. An etching system employed in the invention generally includes beam delivery optics, alignment optics, a high precision and high speed mask shuttle system, and a processing chamber including mechanism for handling and positioning the substrate material.

"Diffusion bonding" refers to a bonding technique which involves the solid-state movement of the atoms and grain growth across a joint interface. Diffusion bonding provides bonded areas which are practically indistinguishable from the adjacent parent metal even on close metallurgical examination. In this regard, reference may be made to the patent to Owczarski et al., U.S. Pat. No. 3,530,568. A particularly preferred technique of diffusion bonding is described herein, wherein the surfaces to be joined are initially electroplated with a very thin surface layer (e.g., approximately 0.0003 inches or less) of nickel, nickel-phosphorous, or a nickel-cobalt alloy. The surface layer is formulated to melt at the desired diffusion bonding temperature, thus forming a transient liquid phase that fills surface defects (irregularities, asperities, and the like) at the interface of the microstructures in the surfaces to be joined. The molten surface layer subsequently re-solidifies, thus eliminating the surface defects.

A "multilayer" integrated assembly refers to an assembly formed from a foldable substrate whereby the component sections are subject to closure so as to form at least two bonded layers. A particularly preferred multilayer integrated assembly includes n component secions and (n−1) linear fold means, wherein n equals three or more, wherein the component sections are closed upon one another in what is referred as a "Z-fold configuration."

An "intermediary substrate" refers to an added substrate layer interposed between the first and second component sections prior to closure and bonding of the first and second component sections so as to provide a composite structure. A "laminate" refers to the resulting multilayer structure, that is, a composite structure formed using a bondable intermediary substrate interposed between the first and second component sections. One particularly preferred intermediary substrate comprises an ultrathin plate, thereby providing a means for producing a laminate having layers of differing thicknesses.

The present invention will find particular application in a variety of analytical systems that benefit from an integrated assembly that supports one or more fluid handling functions with respect to one or more fluid streams. Accordingly, the terms "fluid-handling" and "fluid-handling functions" refer to initiation, distribution, redirection, termination, control, detection, analysis, sensing, treatment, and similar functions with respect to one or more fluid streams.

"Sample treatment" refers to sample preparation chemistries. In particular, an analyte of interest is generally obtained in a matrix containing other species which may potentially interfere with the detection and analysis of the analyte. Accordingly, a sample treatment component is a portion of the sample processing compartment in which analyte separation from the matrix is effected. Examples of fluid handling functions which may be served by the sample treatment component include chromatographic separations, electrophoretic separations, electrochromatographic separations, and the like.

"Detection means" refers to means, structure or configuration which is connectable to the integrated assembly and which allows one to interrogate a sample using analytical detection techniques well known in the art. Thus, a detection means may include one or more apertures, elongated apertures or grooves which are made to communicate with the sample processing compartment; alternatively, the sample detection means may include fittings or connections in the integrated assembly that allows an external detection apparatus or device to be interfaced with the sample processing compartment to detect an analyte passing through the compartment.

Changes in the thermal, electrical, or electrochemical properties of a sample passing through the sample processing compartment can be detected using detection means which physically contact the sample passing through the sample processing compartment. In one embodiment, an electrode may be placed within, or butt-coupled to a detection means such as an aperture or a groove, thereby enabling the electrode to directly contact the sample stream. For example, by arranging two electrodes (which are connected through an external conducting circuit) opposite each other relative to the sample processing compartment, an electric field can be generated in the sample processing compartment—transverse to the direction of sample flow—thereby providing a ready means of electrochemical detection of analytes passing through the compartment. Alternatively, detectable changes in the conductivity, permittivity, or both of a particular sample due to the presence of an analyte in the sample can be detected using an electrometer; using a thermal conductivity detector, changes in the thermal properties of a sample passing through the sample processing compartment can be detected.

"Analysis" refers to detecting and analyzing small and/or macromolecular solutes in the gas or liquid phase and may employ chromatographic separation means, electrophoretic separation means, electrochromatographic separation means, or combinations thereof. The terms "gas phase analysis" and "liquid phase analysis" are respectively used to refer to analyses which are done on either small and/or macromolecular solutes in the gas or liquid phase. Accordingly, "analysis" as used herein includes chromatographic separations, electrophoretic separations, and electrochromatographic separations. Integrated assemblies constructed according to the invention are useful in any analysis system for detecting and analyzing small and/or macromolecular solutes in the gas or liquid phase and may employ chromatographic separation means, electrophoretic separation means, electrochromatographic separation means, or combinations thereof. In this regard, "chromatographic" processes generally comprise preferential separations of components, and include reverse-phase, hydrophobic interaction, ion exchange, molecular sieve chromatography and like methods.

"Fluid" refers to both to gases and liquids, and thus to all types of fluids. The following description of the invention will include a description of the arrangement, construction, or operation of certain fluid-handling devices, and hence is particularly directed to the provision of a plurality of gaseous streams in a gas chromatographic analytical system. However, sample analysis systems that are particularly benefited by use of the present invention include supercritical fluid chromatography, high-pressure gas chromatography (HPGC), liquid chromatographs, high-performance liquid chromatography (HPLC), clinical analyzers, flow-injection analyzers, laboratory water purification systems, syringe-type reagent dispensers, manual and automated solid phase extraction (SPE) instruments, supercritical fluid extraction (SFE) instruments, spectrophotometers, automated protein or nucleic acid sequencers, and solid phase protein or nucleic acid synthesizers.

"Electrophoretic" separations refers to the migration of particles or macromolecules having a net electric charge where said migration is influenced by an electric field. Accordingly electrophoretic separations contemplated for use in the invention include separations performed in columns packed with gels (such as polyacrylamide, agarose and combinations thereof) as well as separations performed in solution. "Electrochromatographic" separation refers to combinations of electrophoretic and chromatographic techniques.

The term "motive force" is used to refer to any means for inducing movement of a sample along a path in a sample analysis system, and includes application of an electric potential across any portion of the path, application of a pressure differential across any portion of the path, or any combination thereof.

The term "surface treatment" is used to refer to preparation or modification of the surface of a component section, and in particular of a channel which will be in contact with a sample during separation, whereby the characteristics of the surface are altered or otherwise enhanced. Accordingly, "surface treatment" as used herein includes: physical surface coatings such as silication or silane coatings; physical surface adsorptions; covalent bonding of selected moieties to functional groups on the surface of channel substrates; methods of coating surfaces, including dynamic deactivation of channel surfaces, substrate grafting to the surface of channel substrates, and thin-film deposition of materials such as diamond or sapphire to channel substrates.

"Optional" or "optionally" means that the subsequently described feature or structure may or may not be present in the embodiment or that the subsequently described event or circumstance may or may not occur, and that the description includes both instances where said feature or structure is present and instances where the feature or structure is absent, or instances where the event or circumstance occurs and instances where it does not.

Referring generally to FIGS. 2–9, as will be appreciated by those working in the field of fluid handling devices, the methods described herein may be used to assemble a wide variety of miniaturized integrated assemblies for effecting fluid-handling functions. In the practice of this invention, a first component section may be arranged over a second component section and, in combination with the fold means, and by closure of the component sections, the complementary microstructures superimposed therein will form, e.g., a fixed channel or compartment. According to the invention, the component sections may be sealed together to form a gas- or liquid-tight fluid handling functional device by using known pressure sealing or bonding techniques, by using external means to urge the pieces together (such as clips, tension springs or associated clamping apparatus), or by using adhesives well known in the art of bonding substrates and the like. In a particularly preferred embodiment, the component sections are hermetically sealed and bonded together via diffusion bonding.

It will be readily appreciated that, although a channel may be represented in a generally extended form, channels formed according to the invention may be etched in a large variety of configurations, such as in a straight, serpentine, spiral, or any tortuous path desired. Further, as described in greater detail below, a channel may be formed in a wide variety of channel geometries including semi-circular, rectangular, rhomboid, and the like, and the channels may be formed in a wide range of aspect ratios. It is also noted that a device having a plurality of channels provided thereon falls within the spirit of the present invention.

Other particular embodiments of the invention further comprise apertures provided so as to communicate with a channel or compartment at a first end thereof to form an inlet port enabling the passage of fluid from an external source into the channel or compartment. A second aperture communicates with the channel or compartment at a second end thereof to form an outlet port enabling passage of fluid from the channel or compartment to an external receptacle.

Figure 2:
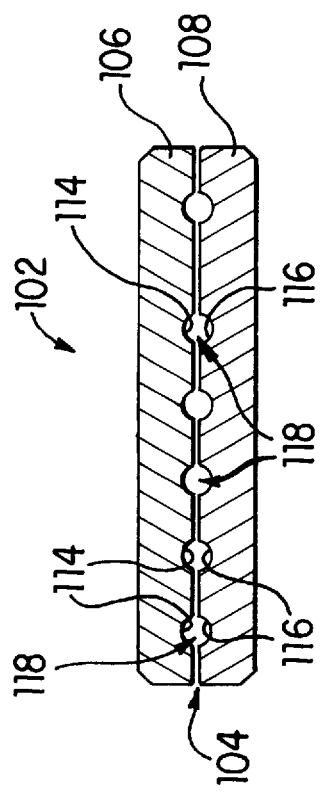
FIG. 2 is a cross-sectional axial view of channels formed by the alignment of complementary microstructures via closure of first and second component sections in a first embodiment of a foldable substrate, whereby closure provides an integrated assembly constructed according to the present invention.

Referring now to FIG. 2, a first embodiment of an integrated assembly for performing one or more of a wide variety of fluid-handling functions is formed as a miniaturized planar device 102 by providing a linear fold means 104 interposed between first and second component halves indicated at 106 and 108 respectively. The support body may comprise a substantially planar foldable substrate such as a metallic plate which is etchable so as to enable the first and second component halves 106 and 108 to each have substantially planar interior surfaces, indicated at 110 and 112 respectively, wherein microstructures and other miniaturized features may be etched. More particularly, a first channel pattern 114 is etched in the first planar interior surface 110 and a second, complementary channel pattern 116 is etched in the second planar interior surface 112. According to the invention, said first and second channel patterns are respectively etched in the first and second component halves 106 and 108 in locations selected according to the location of a fold axis defined by the linear fold means 104, such that the first and second channel patterns are made to be the mirror image of each other about the fold axis. The first and second component halves 106 and 108 are then folded together and diffusion bonded to provide the planar device 102.

Figure 3:
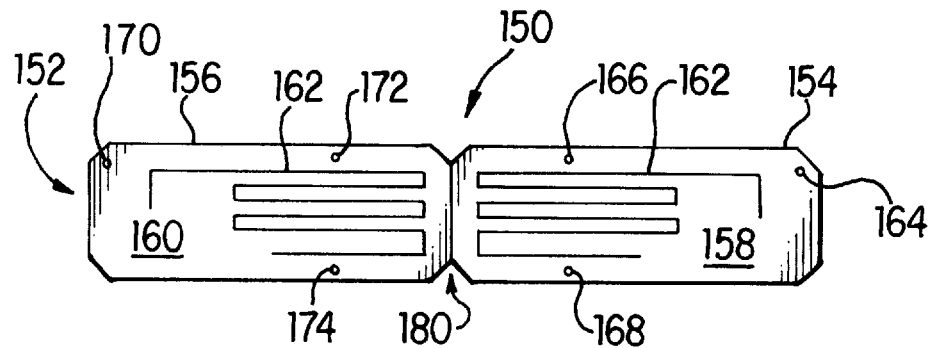
FIG. 3 is a plan view of a preferred embodiment of the foldable substrate of FIG. 2, prior to closure, illustrating first and second complementary microstructures in respective component sections and having linear fold means situated between first and second component sections,.
Figure 4:
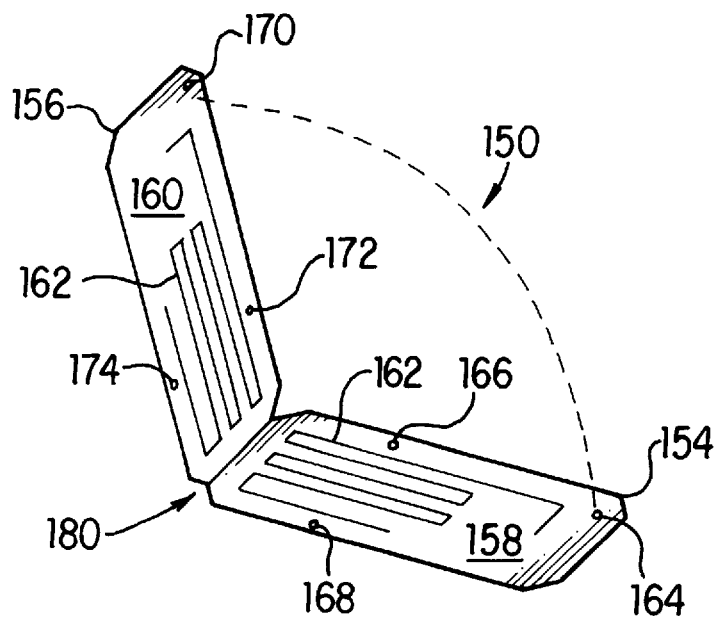
FIG. 4 is a pictorial representation of the foldable substrate of FIG. 3 showing the linear fold means in operation during closure of the component sections.
Figure 5:
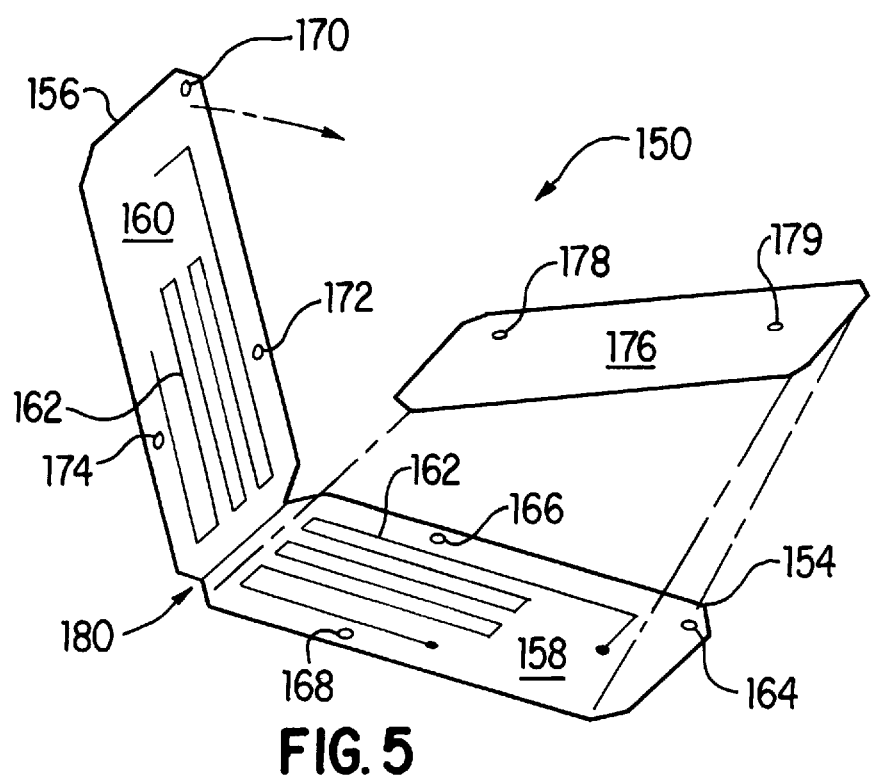
FIG. 5 is an exploded view of the foldable substrate of FIGS. 3 and 4 during closure, but with the addition of a specialized intermediary substrate.

Referring now to FIGS. 3–5, a second embodiment of an integrated assembly constructed according to the present invention is provided in the form of a miniaturized planar device 150 and is formed in a foldable substrate 152. The integrated assembly comprises first and second support body halves, indicated at 154 and 156 respectively, each having a substantially planar interior surface indicated at 158 and 160 respectively. The interior surfaces each comprise one or more complementary microstructures, one of which is generally indicated at 162, where the complementary microstructures are arranged to provide the mirror image of one another with respect to a linear fold means in a manner about to be described. Accordingly, in the practice of the invention, the foldable substrate 152 includes means to allow the first and second support body halves 154 and 156 to superimpose upon one another in a way that accurately aligns composite features defined by the microstructures etched on said first and second planar interior surfaces 158 and 160.

The accurate alignment of microstructures and other surface features in the component sections are enabled by forming such microstructures and features in a foldable substrate 152 having at least one linear fold means, generally indicated at 180, such that a first body half 154 may be folded onto a second body half 156. The linear fold means 180 preferably includes a of spaced-apart perforations located in the foldable substrate 152. Alternatively, the linear means may include spaced-apart, slot-like depressions, grooves, or the like etched so as to extend only part way through the foldable substrate. The perforations or depressions may have circular, diamond, hexagonal or other shapes that promote hinge formation along a predetermined, straight line that constitutes the fold axis.

It is contemplated that the linear fold means allows accurate microalignment of features in a consistent, reliable, and simple fashion, merely by folding first body half 154 onto the second body half 156. However, it is further contemplated that some applications may demand the provision of corroboration means for corroborating the successful establishment of microalignment; accordingly, either by etching or by other methods of fabricating, certain shaped features are provided in the first body half 154 and in the second body half 156 that are designed to physically exhibit the degree of alignment precision and are subject to inspection after closure of the foldable substrate 152. More specifically, a plurality of features 164, 170 may be provided in said first and second support body halves 154 and 156 where said features are so arranged such that co-axial alignment thereof enables corroboration of the precise alignment of the support body halves. For example, the features 164, 170 may be through-holes such that alignment may be corroborated using an external apparatus with means (such as light beam) for cooperating with said co-axial apertures to observe the degree of alignment with one another.

Hence in yet another particular embodiment of the invention, corroboration of microalignment is established by examination of the presence of one or more blocks, one of which is formed in the first body half 154 and is indicated at 164, within a complementary window which may be formed in said second support body half 156, one of which is indicated at 170. Accordingly, as is readily apparent, the block 164 and window 170 in the corroboration means are configured to form corresponding symmetrical or concentric structures with respect to one another, whereby, for example, the block 164 is easily observable by the human eye to be centered within the window 170 when said support body halves are aligned in facing superposition with one another. In this manner, positive and precise confirmation of the alignment of support body halves 154 and 156 is enabled subsequent to closure, thereby confirming the accurate superposition of features defined by the microstructures 162.

A wide variety of corresponding corroboration means may be formed in the subject embodiments without departing from the spirit of the instant invention. Such additional features include any combination of windows and/or corresponding structures such as grooves and ridges, or, for example, dual windows having slightly differing sizes, whereby said features cooperate to enable observation of microalignment of the component sections.

With particular reference to FIG. 5, a specialized intermediary substrate 176 may be interposed between the body halves 154 and 156 such that one or more integral features, generally indicated as 178 or 179 may interface with a feature or microstructure on one of the first and second planar interior surfaces 158 and 160. The intermediary substrate 176 is contemplated as being useful for providing a characteristic that may differ in a useful way from the material used to provide the foldable substrate 152. Accordingly, a intermediary substrate 176 may be included to expand the functionality of the planar device 150. For example, the intermediary substrate 176 can support a feature 178,179 of a type, structure, or function that is difficult or impractical to provide in the foldable substrate 152 but which can be effectively provided in the material used to fabricated the intermediary substrate 176. Examples of such features include structural features such as: a microstructure, conductor, semiconductor, insulator, electrode, sensor, sensor array, catalyst, orifice, screen, well, restriction, frit, perforation, porous section, or permeable or semi-permeable region. Alternatively, the feature 178, 179 may define predetermined region that includes a surface treatment on a particular portion of the surface of the intermediary substrate 176, wherein the feature includes, for example, a surface treatment that is chemically or biologically-active, or includes a surface treatment that exhibits one or more particularly useful physical properties that may be difficult to provide in the foldable substrate 52, such as an optical, electrical, opto-electrical, magneto-optical, or magnetic characteristic. In still another example, the intermediary substrate 176 can exhibit a dimensional characteristic (such as a lesser thickness) or material composition (such as a ceramic material) that differs from the corresponding characteristic in the foldable substrate, or is difficult or impractical to provide in the foldable substrate 152.

Figure 6A:
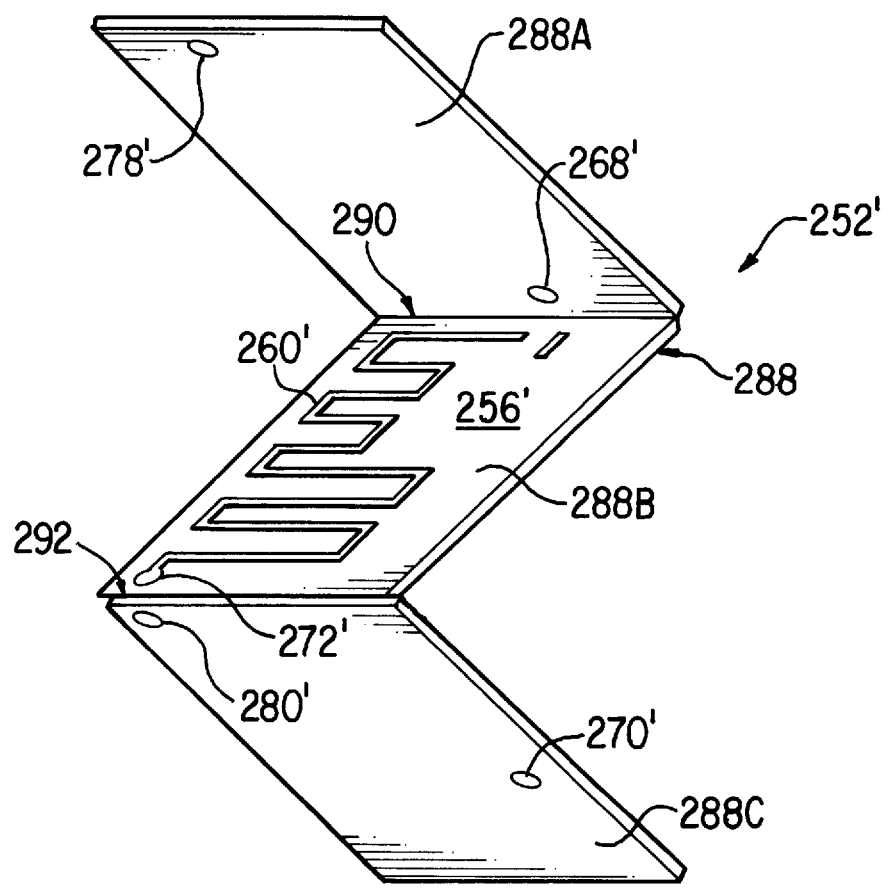
FIG. 6A is a pictorial representation of a first side of a second preferred embodiment of a foldable substrate constructed according to the present invention and which includes a plurality of three or more component sections so as to effect a Z-fold configuration.
Figure 6B:
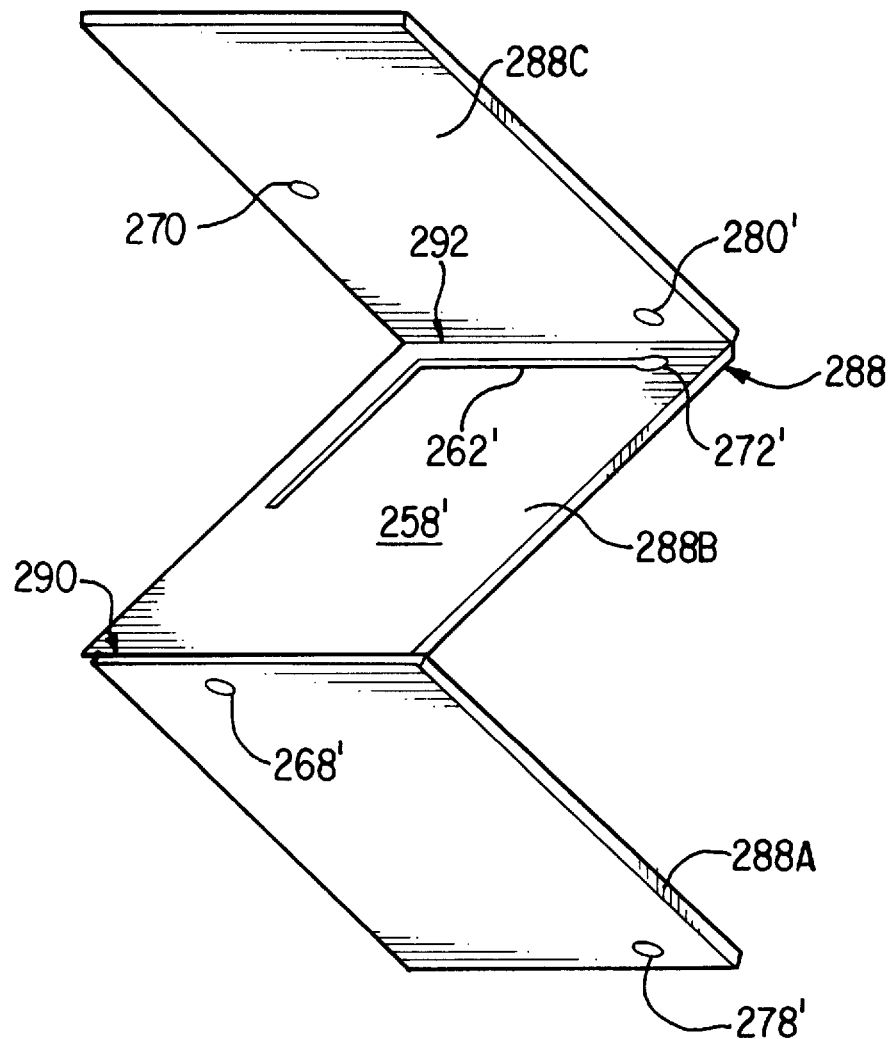
FIG. 6B is a pictorial representation of a second side of the foldable substrate of FIG. 6A.

Referring now to FIGS. 6A and 6B, a third embodiment of an integrated assembly may be provided in the form of a miniaturized planar device 252', wherein n component sections are formed by definition of (n−1) linear fold means in a single foldable substrate generally indicated at 288. In the illustrated embodiment, n is greater than two. The foldable substrate 288 thus comprises at least three component sections, e.g., a first portion 288A, second portion 288B, third portion 288C that may be closed upon one another according to a configuration considered herein as a "Z-fold" configuration. The second portion 288B, having first and second substantially planar opposing surfaces 256' and 258', respectively, where the second portion is interposed between a first portion 288A and a third portion 288C. The first and third portions have at least one substantially planar surface. The first portion 288A and the second portion 288B are separated by at least one linear fold means 290 such that the first portion can be readily folded to overlie the first substantially planar surface 256' of the second portion 288B. The third portion 288C and the second portion 288B are likewise separated by at least one linear fold means 292 such that the third portion can be readily folded to overlie the second substantially planar surface 258' of the second portion 288B. As described hereinabove, in particularly preferred embodiments, each linear fold means 290 and 292 includes a row of spaced-apart perforations etched in the foldable substrate, or spaced-apart slot-like depressions or apertures etched so as to extend only part way through the foldable substrate, or the like. The perforations or depressions can have circular, diamond, hexagonal or other shapes that promote hinge formation along a predetermined straight line.

Thus, the planar device 252' is formed by etching a first channel 260' in the first planar surface 256' of the second portion 288B, and a second channel 262' in the second planar surface 258' of the second portion. Each channel can be provided in a wide variety of geometries, configurations and aspect ratios. A first compartment is then formed by folding the foldable substrate 288 at the first fold means 290 such that the first portion 288A covers the first channel 260' to form an elongate compartment. A second compartment is then provided by folding the foldable substrate 288 at the second fold means 292 such that the third portion 288C covers the second channel 262' to form a compartment as described above. A conduit means 272', comprising an etched aperture in the second portion 288B having an axis which is orthogonal to the first and second planar surfaces 256' and 258', communicates a distal end of the first channel 260' with a first end of the second channel 262' to form a single, extended compartment.

Further, an aperture 268', etched in the first portion 288A, enables fluid communication with the first channel 260', and a second aperture 270', etched in the third portion 288C, enables fluid communication with the second channel 262'. As described above, when the first and second apertures are used as an inlet and outlet port, respectively, a miniaturized fluid-handling device is provided having a flow path extending along the combined length of the first and second channels.

Figure 7:
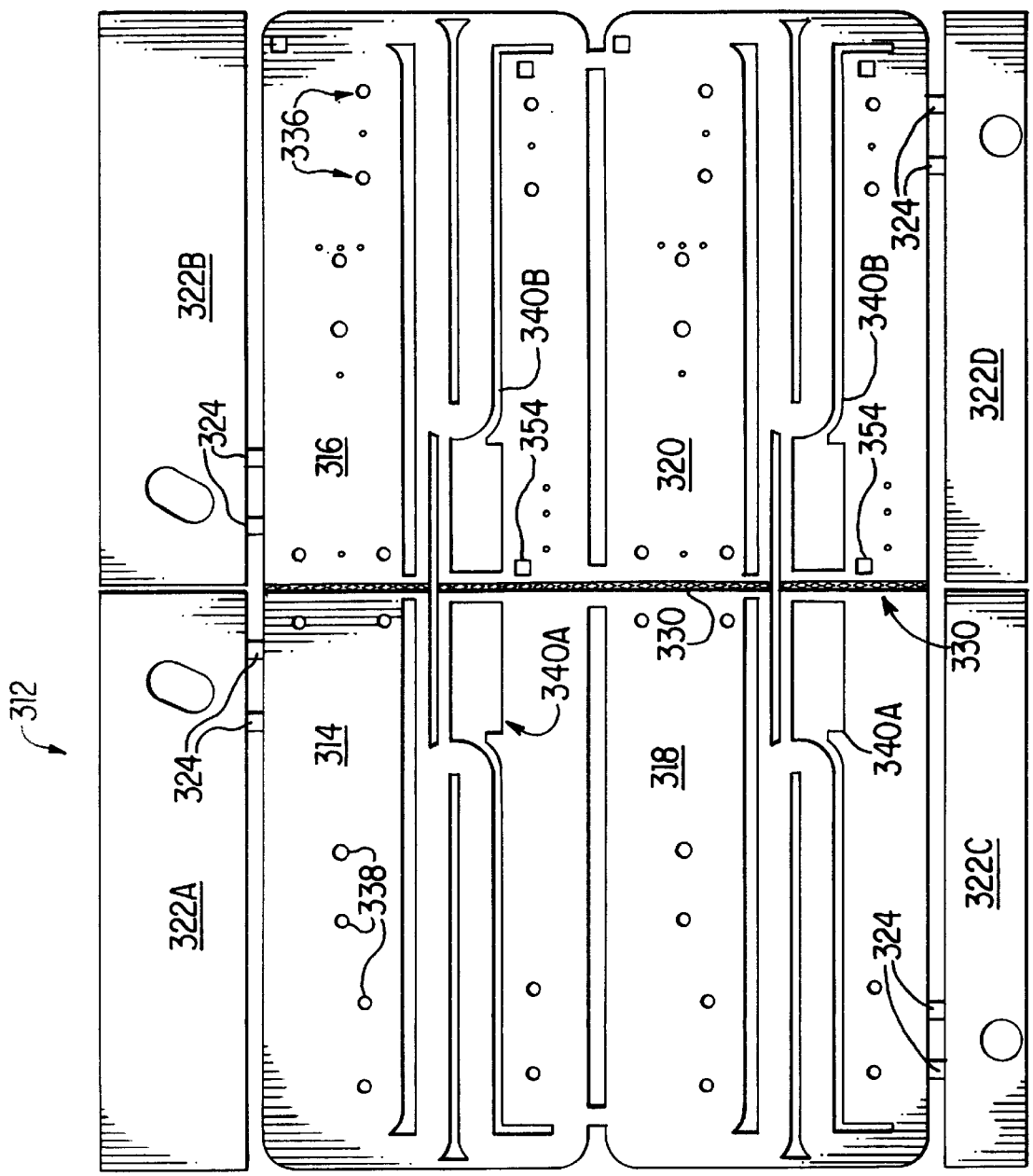
FIG. 7 is a plan view of an exterior side, prior to closure, of a third preferred embodiment of a foldable substrate constructed for use as a miniaturized planar fluid manifold according to the invention.
Figure 8:
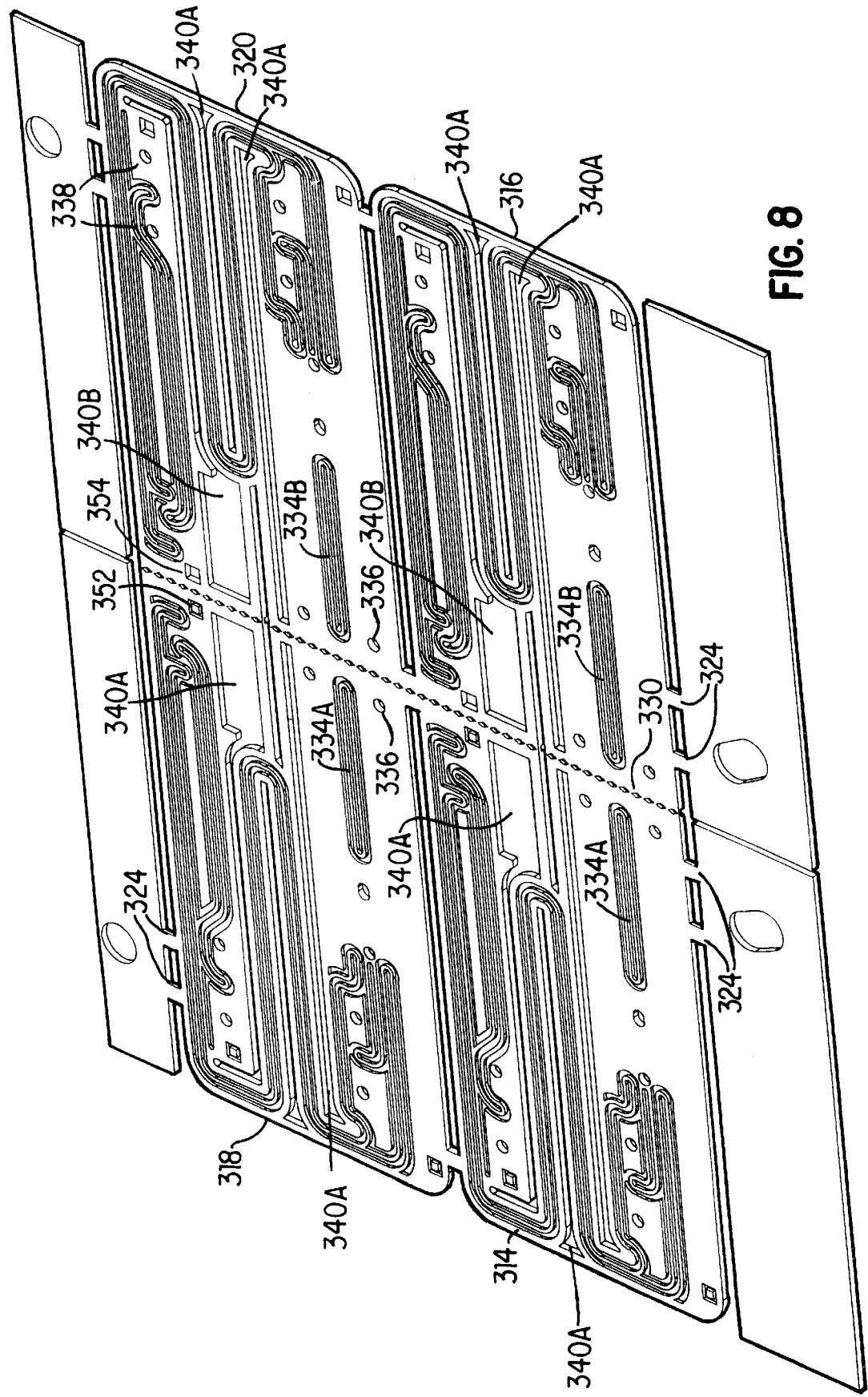
FIG. 8 is a side perspective view of the interior side of the planar fluid manifold of FIG. 7 prior to closure.
Figure 9:
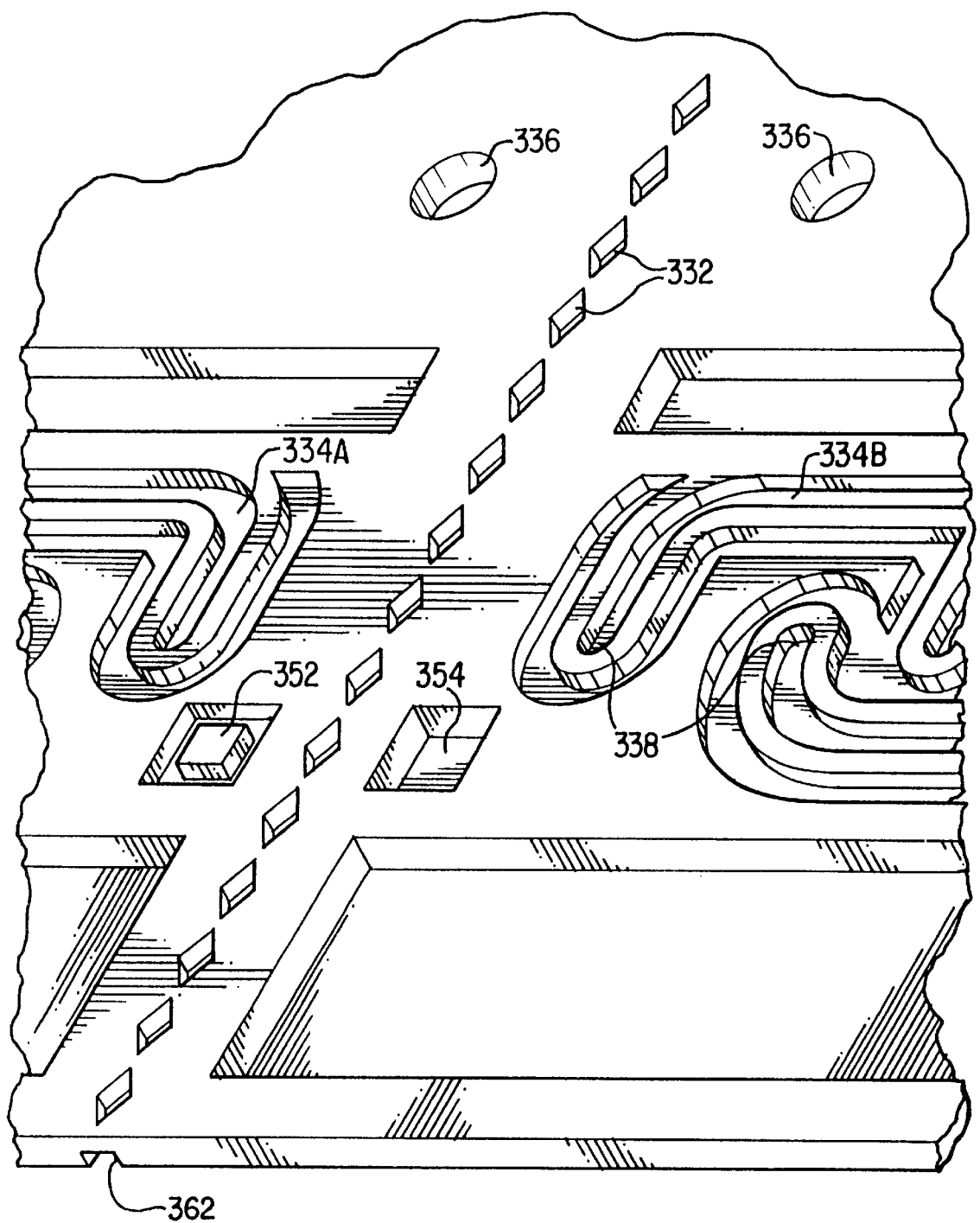
FIG. 9 is a side perspective, detailed view of a central portion of the interior side of the planar fluid manifold of FIG. 7.

With reference now to FIGS. 7–9, a particular embodiment of miniaturized fluid-handling devices constructed according to the present invention will now be described.

As illustrated in FIGS. 7–9, a miniature planar manifold device may be provided in a fourth embodiment of an integrated assembly formed from a foldable substrate 312. In the practice of the invention, miniaturized planar manifold device or a miniaturized planar column device may be formed by etching a set of desired features in the selected foldable substrate to form complementary microstructures. For example, the foldable substrate includes complementary microstructures having micro-capillary dimensions ranging from 50–800 micrometers in diameter and path lengths of up to 15 meters or greater.

With reference to FIG. 7, the foldable substrate 312 includes first and second component sections 314, 316 and optional additional component sections 318, 320. Support tabs 322A, 322B, 322C, 322D may be snapped off of the component sections via breakable links 324 after the assembly process is complete. A variety of etched microstructures are contemplated to include: a linear fold means 330 including a linear arrangement of spaced perforations 332; device mounting holes 336; a variety of apertures 338; complementary microstructures such as channels 334A and 334B; thermal breaks 340A, 340B; and microalignment corroboration means in the form of blocks 352 and windows 354. The linear fold means further includes a preferred embodiment of a fold relief constructed in the form of a groove 362 which underlies the perforations 332. The fold relief allows the component sections 314–320 to fold flat without any significant distortion of the foldable substrate 312 in the vicinity of the linear fold means.

What is claimed is:

1. A multilayer integrated assembly for effecting fluid handling functions, comprising:
a planar foldable substrate having a linear fold means, the linear fold means defining a linear fold axis and at least first and second component sections, wherein said substrate is comprised of a material that is ductile in the region of the linear fold means and substantially inextensible in the regions defined by the component sections, wherein said first and second component sections include respective first and second surface features on respective first and second mating surfaces, wherein the surface features are aligned and superimposed upon folded closure of the planar foldable substrate at the linear fold axis to form a fluid handling functional device in a unitary planar assembly.

2. The integrated assembly of claim 1, further comprising n component sections and (n–1) linear fold means, wherein n equals three or more, and wherein the component sections are closed upon one another in a Z-fold configuration.

3. The integrated assembly of claim 1, wherein the first and second mating surfaces are susceptible to diffusion bonding at a desired diffusion bonding temperature.

4. The integrated assembly of claim 3, wherein at least one of the surface features further includes a surface defect and further comprising a surface layer in at least one of the first and second mating surfaces formulated to melt a the desired diffusion bonding temperature, thus forming an amount of transient liquid phase, whereby the amount of the transient liquid phase fills the surface defect.

5. The integrated assembly of claim 4, wherein the surface defect is located at the interface of the first and second surface features.

6. The integrated assembly of claim 5, wherein the first and second surface features further comprise first and second complementary microstructures.

7. The integrated assembly of claim 5, wherein the first and second surface features further comprise complementary microstructures and wherein the transient liquid phase flows into a surface defect located at the interface of the first and second complementary microstructures.

8. The integrated assembly of claim 3, wherein the foldable substrate further comprises a substrate material selected from the group consisting of: metals, metal alloys, steels, and stainless steel.

9. The integrated assembly of claim 1, wherein the linear fold means includes a fold relief for relieving stress or deformation induced in the substrate in the immediate area of the fold axis during operation of the linear fold means.

10. The integrated assembly of claim 1, further comprising corroboration means for corroborating the alignment of the first and second surface features.

11. The integrated assembly of claim 1, wherein the planar foldable substrate further comprises a surface feature selected from the group consisting of: a microstructure, conductor, semiconductor, insulator, electrode, sensor, sensor array, catalyst, orifice, screen, well, restriction, frit, perforation, porous section, permeable region, and semipermeable region.

12. The integrated assembly of claim 1, wherein the surface treatment is selected from the group consisting of: a chemically-active region, a biologically-active region, and a region having at least one optical, electrical, opto-electrical, magneto-optical, or magnetic characteristic.

13. The integrated assembly of claim 1, wherein an intermediary substrate is interposed between at least two of the component sections.

14. The integrated assembly of claim 13, wherein the intermediary substrate further comprises a surface feature selected from the group consisting of: a microstructure, conductor, semiconductor, insulator, electrode, sensor, sensor array, catalyst, orifice, screen, well, restriction, frit, perforation, porous section, permeable region, and semipermeable region.

15. The integrated assembly of claim 13, wherein the intermediary substrate includes a surface treatment selected from the group consisting of: a chemically-active region, a biologically-active region, and a region having at least one optical, electrical, opto-electrical, magneto-optical, or magnetic characteristic.

16. The integrated assembly of claim 13, wherein at least one of the intermediary substrate and the planar foldable substrate further comprises corroboration means for corroborating the alignment of the intermediary substrate and the planar foldable substrate.

17. The integrated assembly of claim 13, wherein the intermediary substrate and the first and second mating surfaces are susceptible to diffusion bonding at a desired diffusion bonding temperature.

18. The integrated assembly of claim 1, wherein the intermediary substrate further comprises a substrate material that differs from the planar foldable substrate.

19. A multilayer integrated assembly for effecting fluid handling functions for use in a sample analysis system, comprising:
a planar foldable substrate having a linear fold means, the linear fold means defining a linear fold axis and first and second component sections, wherein said substrate is comprised of a material that is ductile in the region of the linear fold means and substantially inextensible in the regions defined by the component sections, wherein said first and second component sections include respective first and second channels on respective first and second mating surfaces, wherein the first and second channels are aligned and superimposed by folding the substrate at the linear fold axis and said first and second mating surfaces are subject to diffusion bonding at a desired diffusion bonding temperature, whereby said aligned and superimposed first and second channels form a conduit having inlet and outlet ends, and wherein said planar foldable substrate in folded form provides a unitary planar assembly, and inlet and outlet apertures respectively communicating with the inlet and outlet ends of the conduit for effecting fluid flow of a sample therein, whereby the integrated assembly is useable for effecting fluid flow in the conduit.

20. The integrated assembly of claim 19, wherein an intermediary substrate is interposed between the first and second component sections.

21. The integrated assembly of claim 20, wherein the intermediary substrate further comprises a surface feature selected from the group consisting of: a microstructure, conductor, semiconductor, insulator, electrode, sensor, sensor array, catalyst, orifice, screen, well, restriction, frit, perforation, porous section, permeable region, and semipermeable region.

22. The integrated assembly of claim 20, wherein the intermediary substrate includes a surface treatment selected from the group consisting of: a chemically-active region, a biologically-active region, and a region having at least one optical, electrical, opto-electrical, magneto-optical, or magnetic characteristic.

23. The integrated assembly of claim 20, wherein at least one of the intermediary substrate and the planar foldable substrate further comprises corroboration means for corroborating the alignment of the intermediary substrate with at least one of the first and second component sections.

24. The integrated assembly of claim 19, wherein the first and second mating surfaces are susceptible to diffusion bonding at a desired diffusion bonding temperature.

25. The integrated assembly of claim 24, further comprising:

a surface feature on at least one of said first and second mating surfaces, wherein the surface feature further includes a surface defect;

each of said first mating surface and second mating surface having a respective surface layer, said respective surface layers being formulated to melt at the desired diffusion bonding temperature, thus forming an amount of transient liquid phase during diffusion bonding, whereby the formation of the amount of the transient liquid phase alters the surface defect.

* * * * *